(12) United States Patent
Martinek (10) Patent No.: US 6,840,953 B2
(45) Date of Patent: Jan. 11, 2005

(54) SUTURE SCREW

(75) Inventor: Jonathan Martinek, Hamden, CT (US)

(73) Assignee: United States Surgical Corporation, Nowalk, CT (US)

( * ) Notice: Subject to any disclaimer, the term of this patent is extended or adjusted under 35 U.S.C. 154(b) by 130 days.

(21) Appl. No.: 10/033,951

(22) Filed: Dec. 22, 2001

(65) Prior Publication Data

US 2002/0147463 A1 Oct. 10, 2002

Related U.S. Application Data

(60) Provisional application No. 60/257,813, filed on Dec. 22, 2000.

(51) Int. Cl.$^7$ .............................................. A61B 17/04
(52) U.S. Cl. ..................................................... 606/232
(58) Field of Search ................................... 606/232, 72

(56) References Cited

U.S. PATENT DOCUMENTS

| | | | |
|---|---|---|---|
| 4,259,072 A | * 3/1981 | Hirabayashi et al. | 433/173 |
| 4,454,875 A | 6/1984 | Pratt et al. | 128/92 B |
| 4,570,623 A | 2/1986 | Ellison et al. | 128/92 B |
| 4,738,255 A | 4/1988 | Goble et al. | 128/92 YF |
| 4,870,957 A | * 10/1989 | Goble et al. | 606/73 |
| 4,895,148 A | * 1/1990 | Bays et al. | 606/213 |
| 5,013,316 A | 5/1991 | Goble et al. | 606/72 |
| 5,122,133 A | * 6/1992 | Evans | 606/73 |
| 5,156,616 A | * 10/1992 | Meadows et al. | 606/232 |
| 5,176,682 A | 1/1993 | Chow | 606/72 |
| 5,258,001 A | 11/1993 | Corman | 606/167 |
| 5,372,599 A | 12/1994 | Martins | 606/75 |
| 5,383,878 A | 1/1995 | Roger et al. | 606/73 |
| 5,417,712 A | 5/1995 | Whittaker et al. | 606/232 |
| 5,472,452 A | 12/1995 | Trott | 606/232 |
| 5,480,403 A | 1/1996 | Lee et al. | 606/232 |
| 5,702,397 A | 12/1997 | Goble et al. | 606/232 |
| 5,733,307 A | 3/1998 | Dinsdale | 606/232 |
| 5,782,866 A | 7/1998 | Wenstrom, Jr. | 606/232 |
| 5,824,011 A | 10/1998 | Stone et al. | 606/232 |
| 5,904,704 A | 5/1999 | Goble et al. | 606/232 |
| 5,911,721 A | 6/1999 | Nicholson et al. | 606/232 |
| 5,941,882 A | 8/1999 | Jammet et al. | 606/73 |
| 5,948,000 A | 9/1999 | Larsen et al. | 606/232 |
| 5,948,001 A | 9/1999 | Larsen | 606/232 |
| 6,096,060 A | 8/2000 | Fitts et al. | 606/232 |
| 6,117,162 A | 9/2000 | Schmieding et al. | 606/232 |
| 6,146,408 A | 11/2000 | Bartlett | 606/232 |
| 6,149,669 A | 11/2000 | Li | 606/232 |

* cited by examiner

Primary Examiner—Gary Jackson (57) ABSTRACT

A two part suture screw for anchoring tissue and bone is disclosed. The suture screw includes a threaded outer sleeve having a longitudinal bore extending therethrough. A pin having a conical insertion tip is provided and includes a proximally extending shaft configured for insertion in the longitudinal bore of the outer sleeve. The shaft includes a transverse bore through the pin for slidingly receiving a length of suture. A pair of channels extend from the transverse bore proximally along the outer surfaces of the shaft. The sleeve is provided with corresponding channels which extend proximally from a point adjacent the throughbore to form a complete bore for free sliding receipt of the suture within the suture screw. The suture contemplated for use with the disclosed suture screw has a diameter smaller than that of the transverse bore and the bores formed by the channels of the pin and sleeve to allow the suture to freely slide therein. A method of using the suture anchor to anchor tissue to bone is also disclosed.

4 Claims, 8 Drawing Sheets

SUTURE SCREW

CROSS REFERENCE TO RELATED APPLICATIONS

This application claims priority to U.S. Provisional Application Ser. No. 60/257,813, filed Dec. 22, 2000, and entitled SUTURE SCREW.

BACKGROUND

1. Technical Field

The present disclosure relates to suture anchors and, more particularly, to self-tapping screw type suture anchors and methods of use.

2. Background of Related Art

During surgery it is often necessary to attach prosthetic implants or soft tissue such as muscle tissue, ligaments, or tendons to hard tissue such as bone. Various types of surgical fasteners are employed for accomplishing this function, including staples, screw and washer systems, suture anchoring devices, and tissue anchors.

The first of these types is illustrated in U.S. Pat. Nos. 4,454,875 and 4,570,623, which show metal staples with spikes on the underside of the crosspiece to secure ligaments.

Fasteners included in the second of these types are available as screw-washer combinations wherein the screw is fabricated from a surgically suitable metal, such as titanium or stainless steel alloy, and is usually of self-tapping design. Suture anchors are adapted to be inserted into predrilled holes in bone and can be made of bioabsorbable material. When securing a ligament or suture within a bore drilled in bone, the self tapping screws may abrade the ligament or suture if the ligament or suture is positioned adjacent the screw within the bore as the screw is threaded into the bone.

Suture anchors are also used to draw tissue adjacent bone. The anchor, having a first end and a suture fixedly attached thereto, is anchored in bone and a second end of the suture is threaded through tissue and a knot is tied to secure the tissue to bone.

What is needed is a suture screw capable of freely receiving lengths of suture material therein so as to draw tissue adjacent bone and/or provide the ability to add or substitute suture material after the suture screw has been positioned within the bone.

SUMMARY

A two part suture screw for anchoring tissue and bone is disclosed. The suture screw includes a threaded outer sleeve having a longitudinal bore extending therethrough. Preferably a distal end of the sleeve threads are interrupted to form cutting edges making the suture screw self-tapping. The longitudinal bore has a hexagonal shape and includes a countersunk portion at its proximal end to receive an insertion tool.

A pin having a conical insertion tip is provided and includes a proximally extending shaft configured for insertion in the longitudinal bore of the outer sleeve. An insertion tip of the pin preferably has a smooth conical surface to ease insertion in a pilot hole in bone. Proximal interrupted cutting threads may be formed on the insertion tip and mate with the interrupted threads on the sleeve. The shaft includes at least one transverse bore though the pin for slidingly receiving a length of suture.

A pair of channels extend from the transverse bore proximally along the outer surfaces of the shaft forming half a suture receiving channel. The sleeve is provided with corresponding channels which extend proximally from a point adjacent the throughbore in the pin to form a complete bore for free sliding receipt of the suture within the suture screw. The suture contemplated for use with the disclosed suture screw has a diameter smaller than that of the transverse bore and the bores formed by the channels of the pin and sleeve to allow the suture to freely slide therein.

A method of using the suture anchor to anchor tissue to bone is also disclosed and includes providing the disclosed suture screw with a length of suture slidably positioned within the throughbore and channels. The self-tapping suture screw is threaded into bone, preferably with the assistance of a pilot hole drilled in the bone. A free end of the suture is affixed to tissue and the opposite end of the suture tensioned to draw the tissue against the bone. The suture can then be tied off or passed back through the tissue and tied off to secure the tissue to bone.

BRIEF DESCRIPTION OF THE DRAWINGS

Various embodiments are described below with reference to the drawings wherein.

DETAILED DESCRIPTION OF PREFERRED EMBODIMENTS

The preferred embodiments of the device and methods disclosed herein are applicable to a wide variety of procedures including, but not limited to, tissue to bone fastening, ligament repair, joint repair or replacement, non-union fractures, facial reconstruction, etc. In addition, it is believed that the present device finds application in both open and minimally invasive procedures wherein access to the surgical site is achieved through a cannula or small incision.

In the description which follows, the term "proximal", as is traditional, will refer to the portion of the device or structure which is closest to the operator or user, while the term "distal" refers to the portion which is further from the user.

The device and method described herein is specifically configured for self-tapping into hard structure, such as bone, and slidably receiving lengths of suture material so as to draw tissue, affixed to one end of the suture material, adjacent the suture screw. Additionally, the ability to slidably receive suture material allows the addition or exchange of one type of suture material for another.

Figure 1:
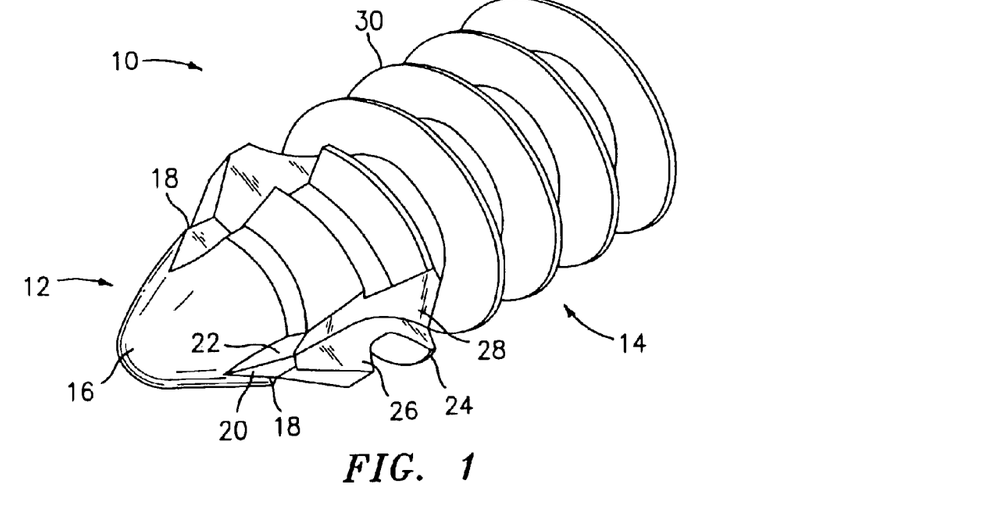
FIG. 1 is a perspective view of a self-tapping two part suture screw.

Referring now to FIG. 1, suture screw 10 includes a pin component 12 and a sleeve component 14 extending proximally from pin component 12. Pin component 12 and/or sleeve component 14 are preferably formed of a biocompatible material. The Material may be bioabsorbable, nonbioabsorbable, an allograft or a xenograft. Suitable bioabsorbable materials include glycolide, lactide, trimethilene carbonate, dioxanone, dioxatanone, and copolymers and blends thereof. Suitable nonbioabsorbable materials include polypropylene, polyethylene, and metals. Pin component 12 has a smooth conical distal tip 16 and interrupted threads 18. Interrupted threads 18 are separated by opposing faces 20 and 22. Faces 20 and 22 form cutting surfaces which allow distal tip 16 of pin component 12 to be self-tapping with respect to hard structure such as, for example, bone.

Sleeve component 14 also has interrupted threads 24 at a distal end thereof which are separated by opposing faces 26 and 28 which allow the distal end of sleeve component 14 to be self-tapping. Sleeve component 14 also includes a continuous thread 30 on the outer surface thereof. Thread 30 extends from a proximal end of interrupted thread 24 to a proximal end of sleeve component 14. As shown, when assembled, interrupted threads 18 of pin component 12 match with the interrupted threads 24 of sleeve component 14.

Figure 2:
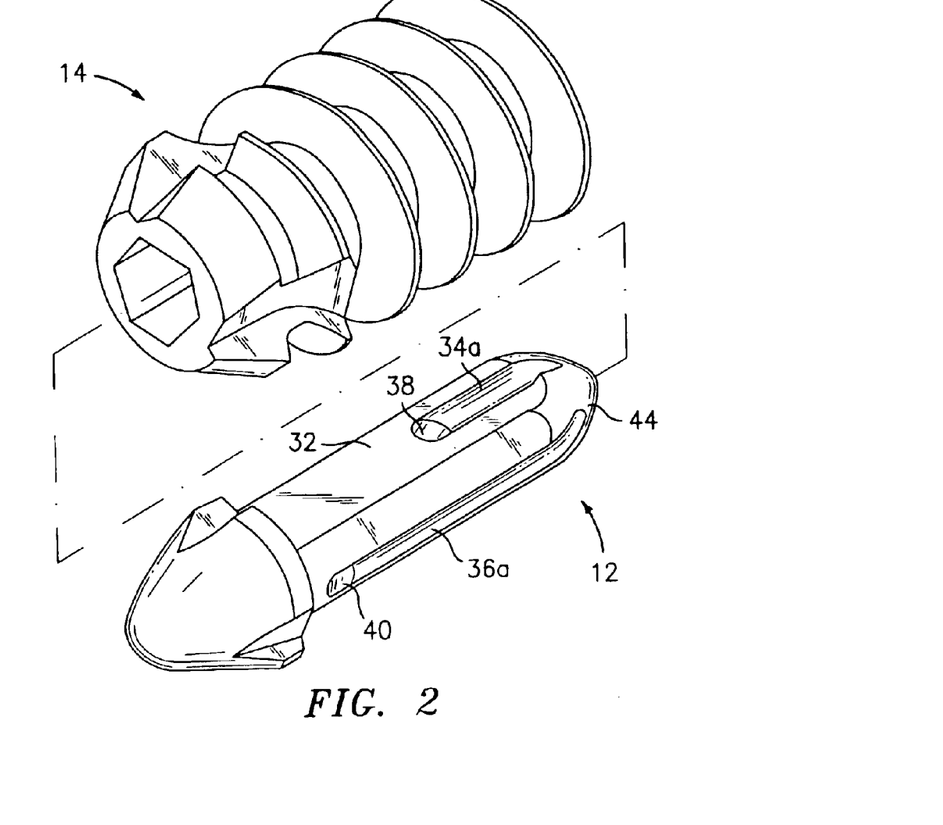
FIG. 2 is a perspective view of the two part suture screw with parts separated.
Figures 3, 4, 5:
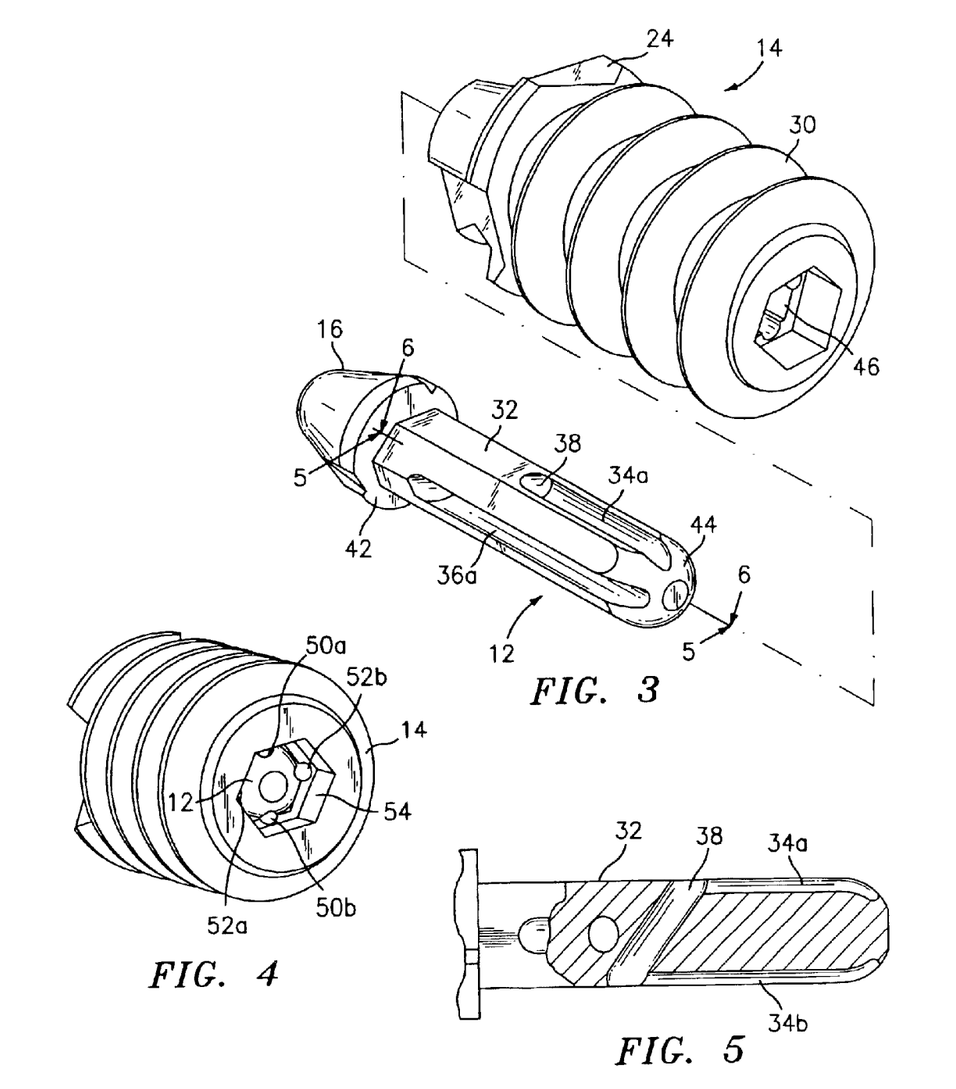
FIG. 3 is another perspective view of the two part suture screw with parts separated.
FIG. 4 is a rear perspective view of a first embodiment of the assembled sleeve component and pin component of the suture screw.
FIG. 5 is a side view, partially shown in section, of the pin component taken along line 5—5 of FIG. 3.
Figure 6:
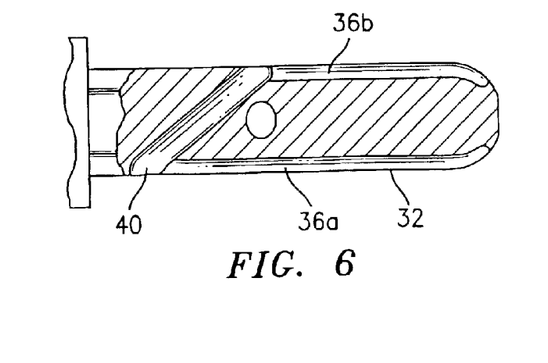
FIG. 6 is a side view, partially shown in section, taken along line 6—6 of FIG. 3.

Referring to FIGS. 2 and 3, pin component 12 includes an elongated shaft 32 extending and channels 36a and 36b are connected by a transverse bore 40 through a different face or part of shaft 32. Preferably transverse bores 38 and 40 are angled in a proximal/distal direction relative to the longitudinal axis of the shaft. Additionally, bores 38 and 40 are angled relative to each other. Channels 34a, 34b and 36a, 36b are preferably semi cylindrical and of greater diameter than the largest diameter suture to be used therein. Similarly, transverse bores 38 and 40 are also of a greater diameter than the largest suture to be used therein. Thus, the sutures used with suture screw 10 are freely slidable therein. While the cross section of shaft 32 is shown to be hexagonal, other configurations of cross sections, such as, for example, oval square, are also contemplated. The non-circular cross sections prevent rotation of pin 12 relative to sleeve 14 during insertion into bone.

Tip 16 of pin component 12 has a flat face 42 at a proximal end thereof which mates flush with a similar flat face on a distal end of sleeve component 14. Pin component 12 also has a chamfered or rounded proximal end 44 to prevent fraying of sutures.

Referring now to FIG. 3, sleeve component 14 is shown with interrupted threads 24 and continuous threads 30. Sleeve component 14 has a longitudinal throughbore 46 having a hexagonal cross section for receipt of elongated shaft 32 of pin component 12. When assembled, a flat distal face 48 of sleeve component 14 mates flush with flat face 42 of pin component 12.

Referring now to FIG. 4, there is shown a rear perspective view of assembled pin component 12 and sleeve component 14. Sleeve component 14 includes opposed pairs of semi cylindrical channels 50a, 50b and 52a, 52b which are complementary to channels 34a, 34b and 36a, 36b to form cylindrical longitudinal bores in a distal section of assembled suture screw 10. Preferably, the bores so formed are of a constant diameter larger than the largest suture to be used there through. Sleeve component 14 has an enlarged countersunk hexagonal bore 54 configured to receive and mate with a driver tip of an installation tool for driving suture screw 10 into bone. In this embodiment, it is envisioned that the sutures running through suture screw 10 would pass through a hollow bore in the tip of the installation tool and out of the tool so as to be freely manipulated.

Figures 7, 8:
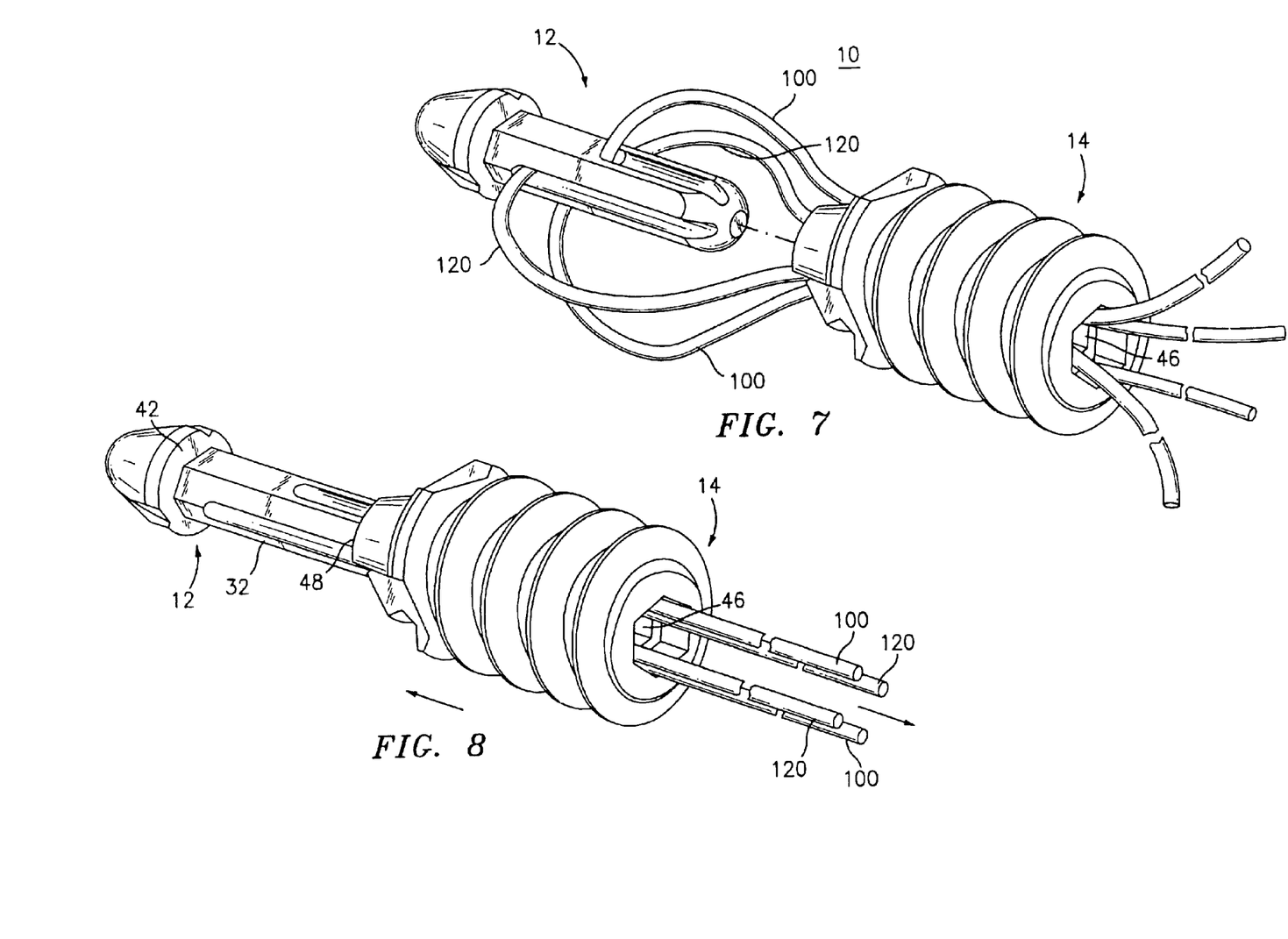
FIG. 7 is a perspective view of the two part suture screw being assembled with lengths of suture.
FIG. 8 is a perspective view similar to FIG. 7 with tension on the sutures.

The use of suture screw 10 to secure a tissue section adjacent a portion of bone will now be described. The desired location on the bone to which the tissue section is to be secured is located and appropriately prepared by scraping, etc. It may be helpful to form a small diameter pilot hole into which screw 10 can be threaded. Referring to FIG. 7, suture screw 10 is prepared by disassembling pin component 12 from sleeve component 14. Sutures 100 and 120 are then threaded through bores 30 and/or 40 and the sutures are positioned in channels 34a, 34b and 36a, 36b. The free ends of the sutures are threaded through longitudinal throughbore 46 of sleeve component 14 and pin component 12.

Referring to FIG. 8, sleeve component 14 and pin component 12 are assembled by inserting shaft 32 into longitudinal throughbore 46 until flat faces 42, 48 meet flush. Care should be taken to ensure channels 50a, 50b and 52a, 52b align with the corresponding channels in pin component 12 so that the sutures remain freely slidable within suture screw 10.

Figure 9:
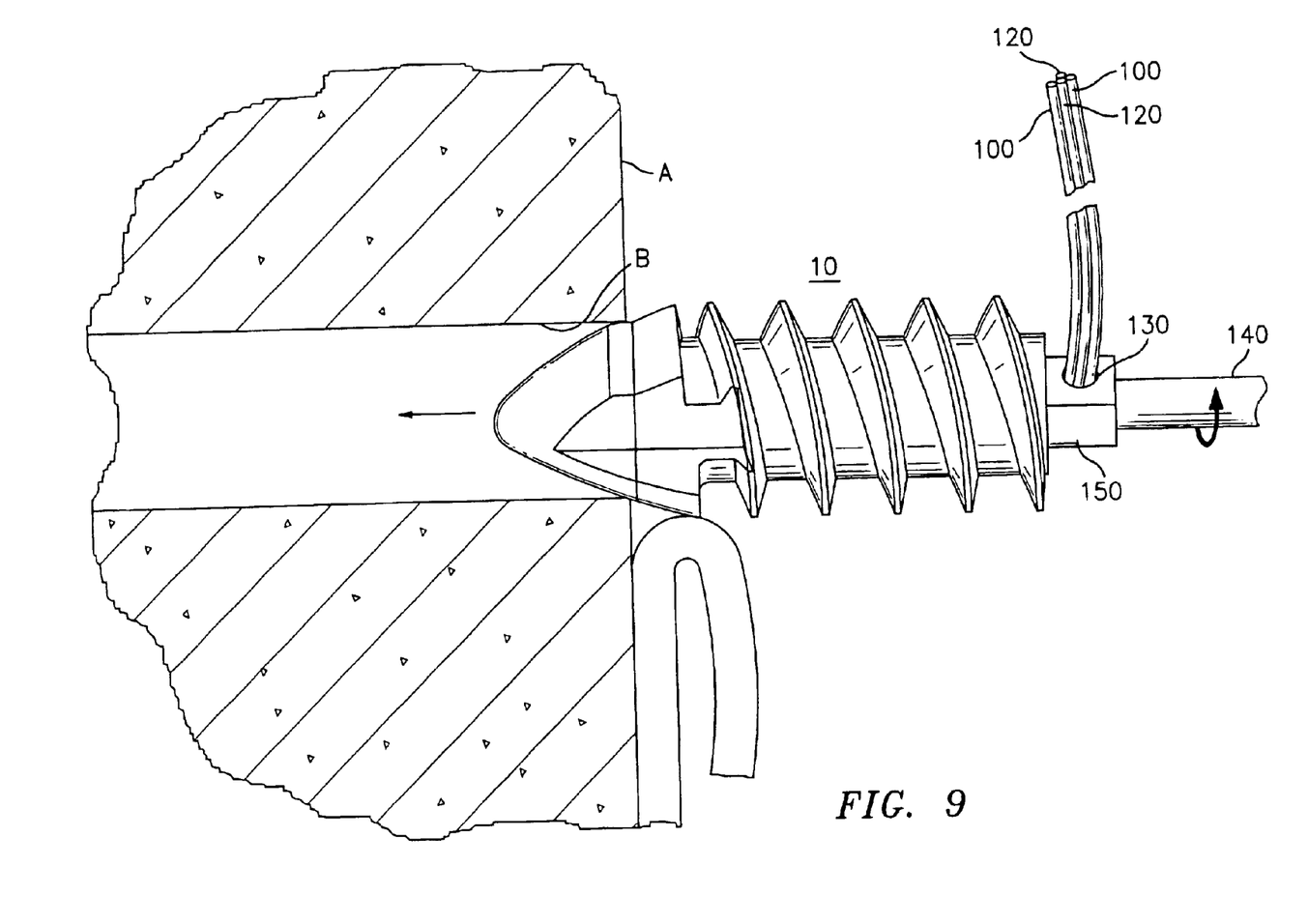
FIG. 9 is a side view of the assembled two part suture screw being inserted in a pilot hole in bone.

Referring to FIG. 9, the free ends of the sutures 100, 120 are then passed through a bore 130 in installation tool 140 and a hexagonal tip 150 of tool 140 is positioned in hexagonal counter bore 54 of sleeve component 14. Proximal tension on the sutures and distal pressure on sleeve component 14 by the installation tool help maintain suture screw 10 in its assembled state. The installation tool is then used to drive suture screw 10 into a predrilled pilot hole B in bone A.

Figure 10:
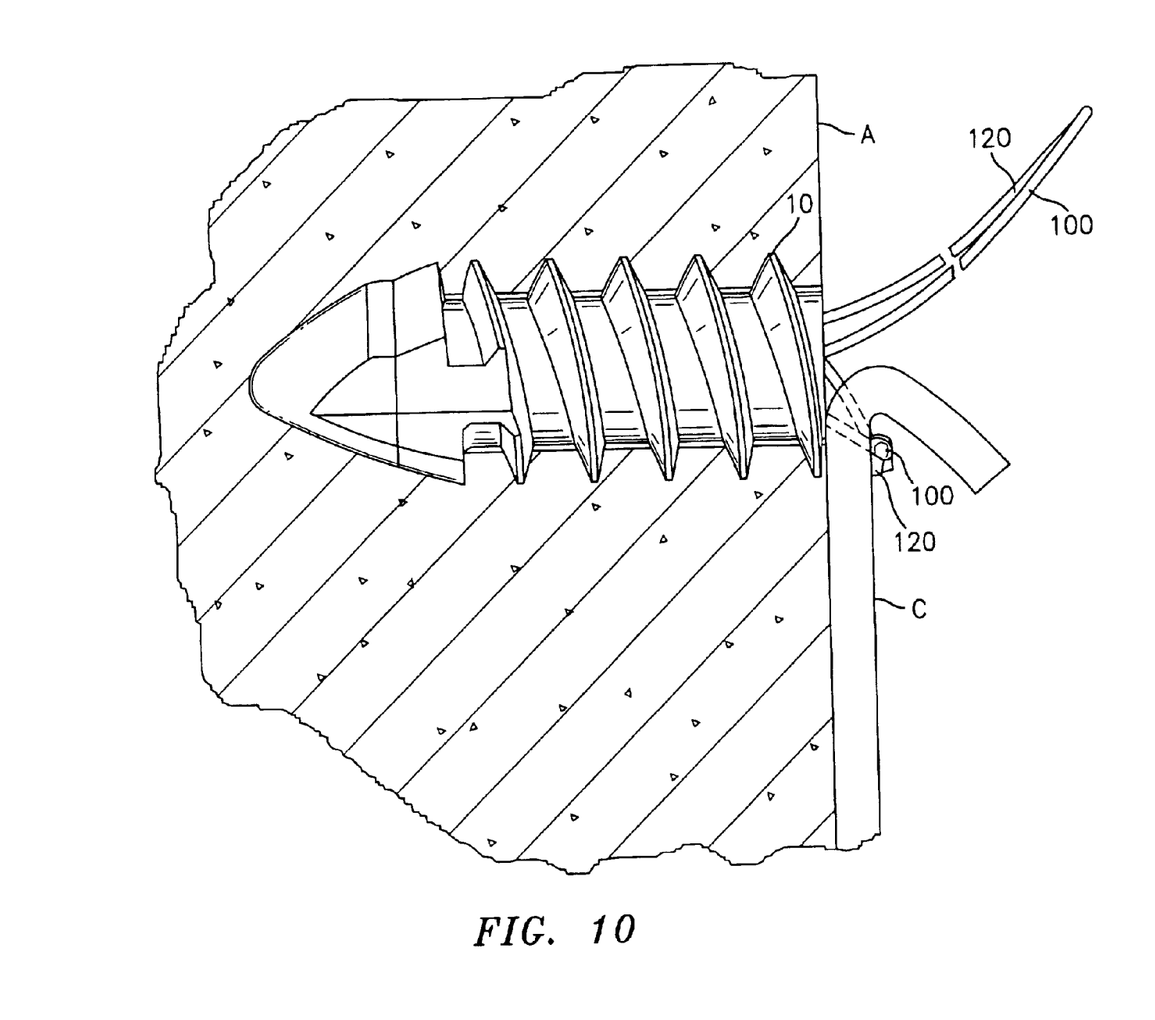
FIG. 10 is a side view of the suture screw fully seated in the bone.
Figure 11:
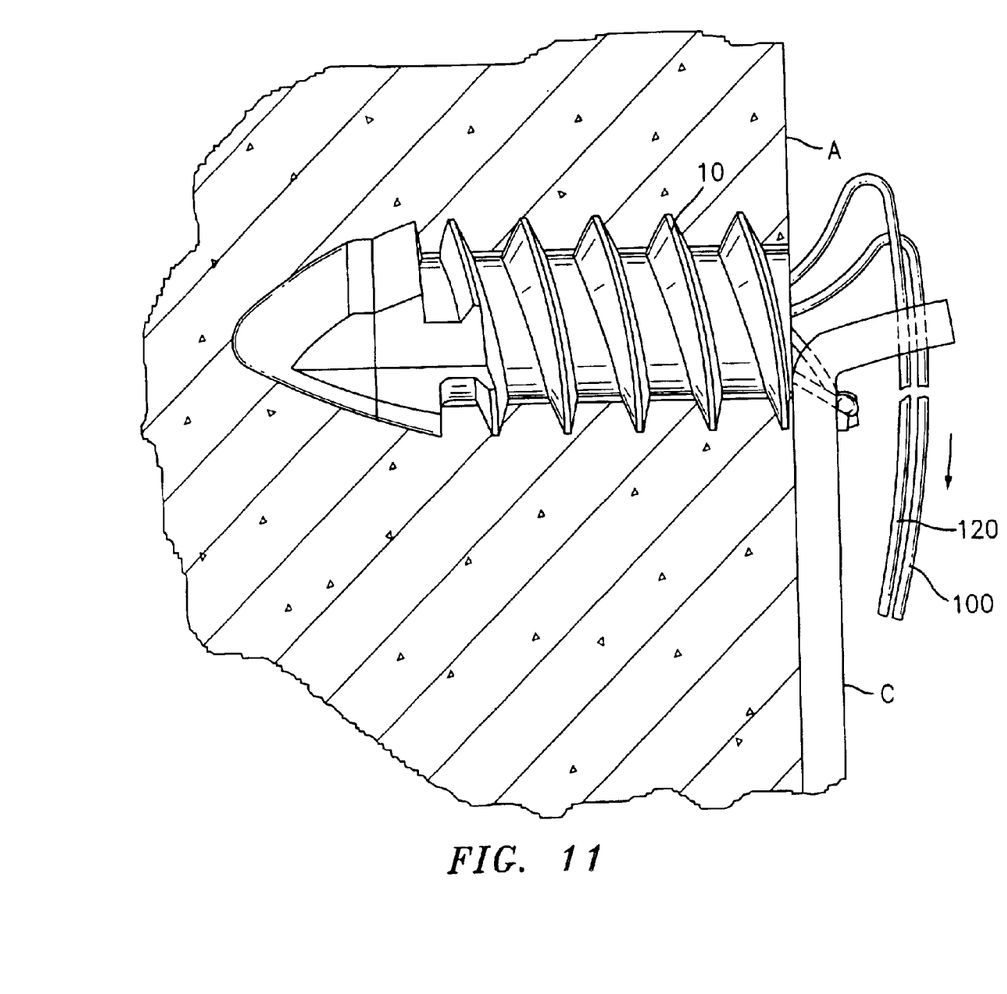
FIG. 11 is a side view of the suture being passed back through tissue.
Figure 12:
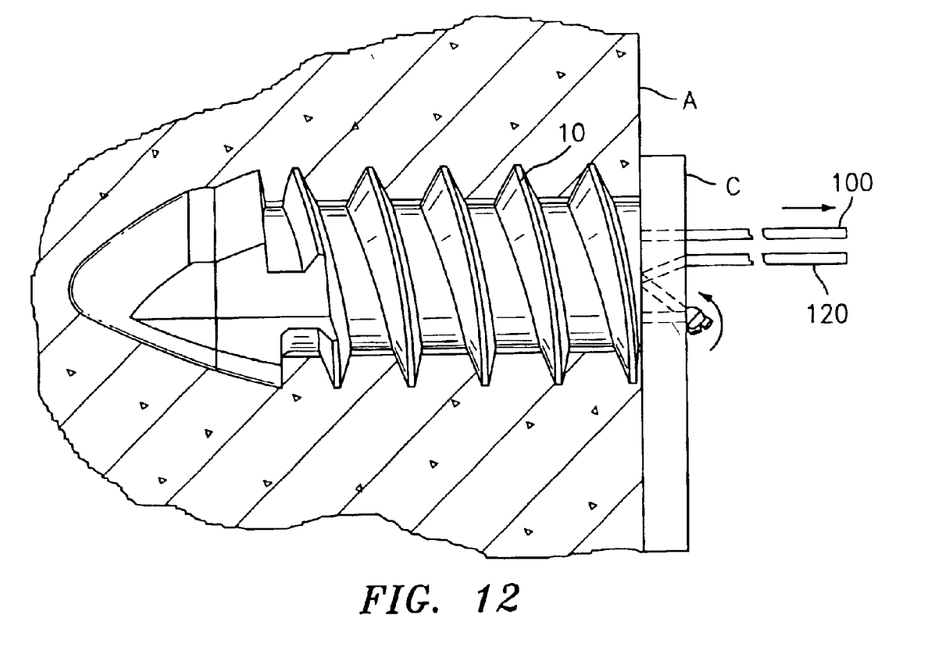
FIG. 12 is a side view similar to FIG. 11 with the suture tensioned.
Figure 13:
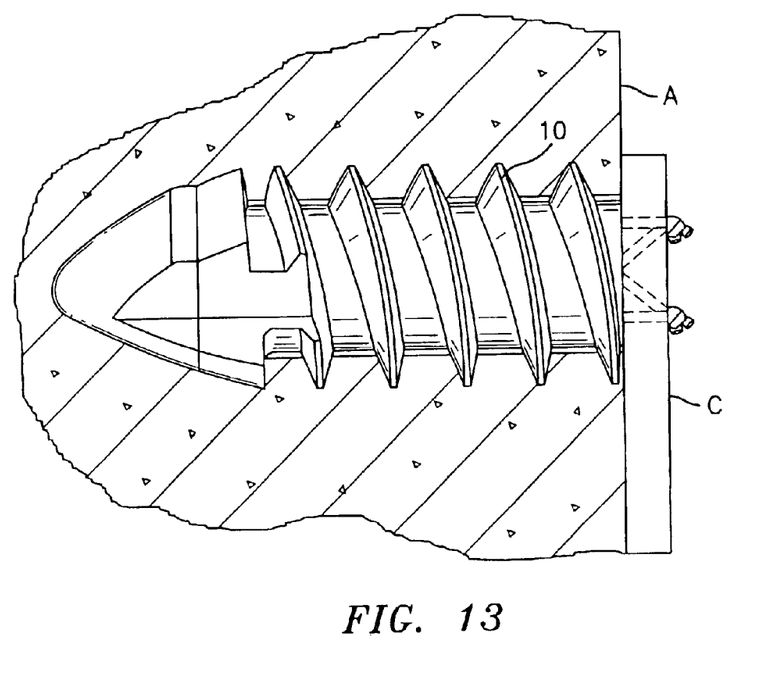
FIG. 13 is a side view of the suture screw and suture tied to anchor and the tissue to the bone.

Referring to FIG. 10, as discussed above, suture screw 10 is self-tapping. When suture screw 10 has been fully inserted in bone B, installation tool 140 is removed and one set of the free ends of sutures 100, 120 are affixed to tissue C. Thereafter, the opposing free ends of the sutures not attached to tissue are tensioned or pulled through suture screw to draw the attached tissue adjacent the bone. Alternatively, additional or substitute suture material of the same or differing type may be attached to the original sutures and pulled into and through suture screw 10 to provide more or a different type of suture for attachment to the tissue section. Once the tissue section has been properly positioned adjacent the bone the opposing ends of sutures may be tied off adjacent the proximal end of suture screw 10 in known manner or otherwise secured adjacent screw 10 and the remaining excess suture material trimmed. Preferably, sutures 100, 120 are reinserted through tissue C (FIG. 11), tensioned to draw tissue C tight (FIG. 12) and tied off FIG. 134 to secure the tissue to bone A.

Figure 14:
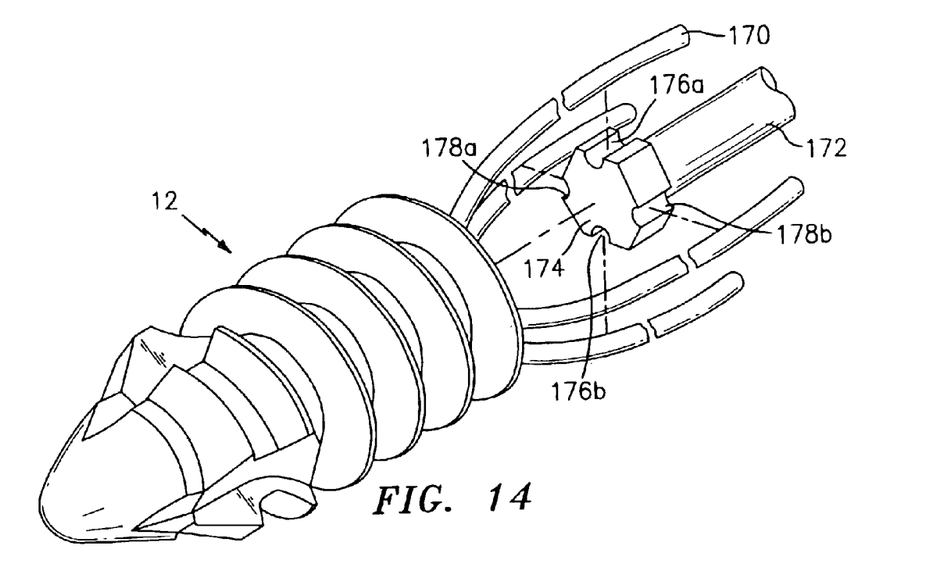
FIG. 14 is a perspective view of the suture screw and an insertion tool.

Referring to FIG. 14, there is disclosed an alternative driving tool 120 for use with suture screw 10, tool 170 includes a proximal shaft 172 and a distal hexagonal driving head 174 to fit in countersunk bore 54 of sleeve component 12. Cutouts 176a, 176b and 1768a, 178b are provided for suture clearance.

Figure 15:
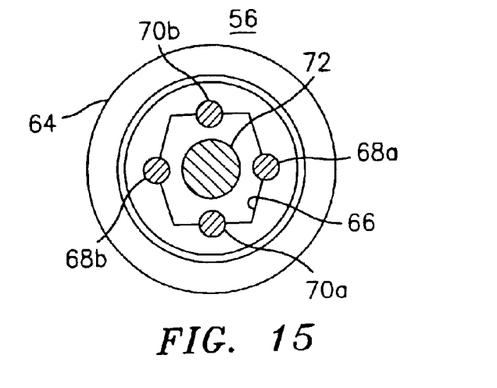
FIG. 15 is a rear end view of a second embodiment of the sleeve component of the suture screw.

Referring now to FIG. 15, there is shown an alternate sleeve component 56 having interrupted threads 58 (not shown) separated by faces 60, 62 (not shown) and continuous thread 64 along a proximal section thereof similar to that of sleeve component 14. Sleeve component 56 also has a hexagonal longitudinal bore 66 which extends completely through sleeve component 56. In contrast to sleeve component 14, sleeve component 56 does not have a countersunk bore and includes channels 68a, 68b and 70a, 70b which extend completely along the inner surface of bore 66. Similar to that of sleeve component 14. Channels 68a, 68b and 70a, 70b cooperate with the corresponding channels in pin component 12 to form bores for sliding receipt of sutures. It is envisioned that the installation tool used with sleeve component 56 would have a corresponding hexagonal shaped driving tip for driving insertion in bore 66. To allow sutures to remain slidable, it would be necessary to form complimentary channels in the outer surface of the installation tool tip.

Figure 16:
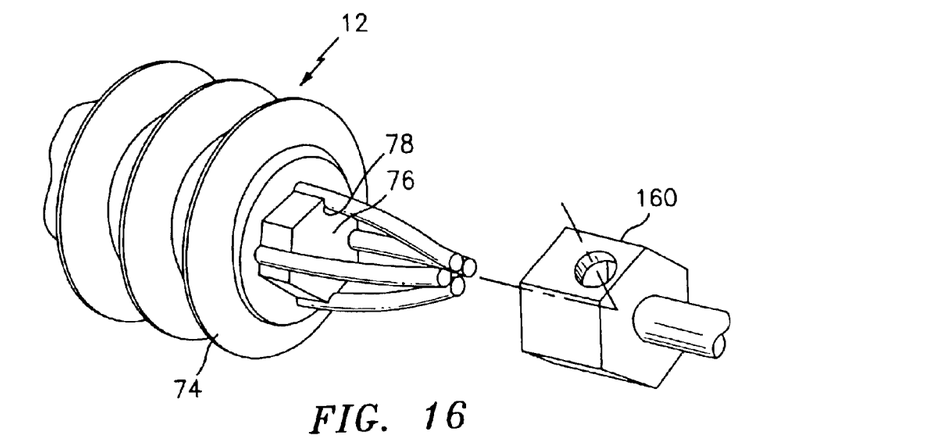
FIG. 16 is a perspective view of a self-tapping suture screw with a third embodiment of a sleeve component.

Referring now to FIG. 16, there is disclosed an alternative embodiment of an assembled suture screw 72. Suture screw 72 utilizes pin component 12 but has an alternative embodiment of a sleeve component 74. Sleeve component 74 has similar outer surface characteristics as previously described sleeve components but has a proximal hexagonal shaped projection 76 for engagement with driver tool 160. As shown, suture channels 78 etc. extend along the outer surface of projection 76 for free receipt of sutures positioned therein.

Alternatively, a modified pin component having an elongated proximally extending shaft, having suture channels, could be assembled with a corresponding sleeve component such that the proximal end of the shaft extends proximally out of the proximal end of the sleeve component.

It will be understood that various modifications may be made to the embodiments disclosed herein. For example, the threads of the pin and/or sleeve component may be partially or completely threaded or continuous. Additionally, there may be provided only a single pair of channels and accompanying through bore or many complimentary pairs greater than the two disclosed. As discussed, the connecting and driving hexagonal bores may be substituted by bores of other cross sections as well as providing corresponding substitute driving tools. The above description should not be construed as limiting, but merely as exemplifications of preferred embodiments and methods. Those skilled in the art will envision other modifications and uses within the scope and spirit of the claims appended hereto.

What is claimed is:

1. A suture screw comprising:

a sleeve having a threaded outer surface and a longitudinal bore, the threads of the sleeve being interrupted at the distal end of sleeve; and a pin having a tip and a shaft extending proximally from the tip, the tip of the pin having interrupted threads formed in an outer surface thereof, the shaft having at least one transverse bore extending from a first side of the shaft to a second side of the shaft, wherein the shaft is positioned within the longitudinal bore of the sleeve.

2. A suture screw for receipt of a length of suture to secure tissue to bone comprising:

a non-expandable outer sleeve having a longitudinal bore there through, the longitudinal bore having a predetermined cross-sectional shape; and a pin having a distal tip, the distal tip of the pin having interrupted threads formed in an outer surface thereof, and a shaft extending proximally from the tin and has a cross-sectional shave similar to the cross-sectional shape of the throughbore such that when the shaft is inserted into the throughbore, there is a minimal rotation between the pin and the sleeve, wherein the pin includes a transverse bore formed through the shaft for receipt of a length of suture.

3. The suture screw as recited in claim 2, wherein an inner surface of the throughbore and an outer surface of the shaft are formed with complimentary longitudinal channels extending from the throughbore proximally toward proximal ends of the pin and the sleeve.

4. A suture screw for receipt of a length of suture to secure tissue to bone comprising:

a non-expandable outer sleeve having a longitudinal bore there through, the longitudinal bore having a predetermined cross-sectional shape; and a pin having a distal tip, the distal tip of the pin having interrupted threads formed in an outer surface thereof, and a shaft extending proximally from the tip and has a cross-sectional shape similar to the cross-sectional shape of the throughbore such that when the shaft is inserted into the throughbore, there is a minimal rotation between the pin and the sleeve, wherein a portion of the outer surface of the tip is smooth and conical.

* * * * *

UNITED STATES PATENT AND TRADEMARK OFFICE
CERTIFICATE OF CORRECTION

PATENT NO. : 6,840,953 B2
APPLICATION NO. : 10/033951
DATED : January 11, 2005
INVENTOR(S) : Jonathan Martinek Page 1 of 1

It is certified that error appears in the above-identified patent and that said Letters Patent is hereby corrected as shown below:

Claim 2:

Line 9, "a cross-sectional shave"

should read

-- a cross-sectional shape --.

Signed and Sealed this

First Day of July, 2008

JON W. DUDAS
*Director of the United States Patent and Trademark Office*

UNITED STATES PATENT AND TRADEMARK OFFICE
CERTIFICATE OF CORRECTION

PATENT NO. : 6,840,953 B2
APPLICATION NO. : 10/033951
DATED : January 11, 2005
INVENTOR(S) : Jonathan Martinek Page 1 of 1

It is certified that error appears in the above-identified patent and that said Letters Patent is hereby corrected as shown below:

Column 6, Claim 2:

Line 26, "a cross-sectional shave"

should read

-- a cross-sectional shape --.

This certificate supersedes the Certificate of Correction issued July 1, 2008.

Signed and Sealed this

Twenty-second Day of July, 2008

JON W. DUDAS
*Director of the United States Patent and Trademark Office*

UNITED STATES PATENT AND TRADEMARK OFFICE
CERTIFICATE OF CORRECTION

PATENT NO. : 6,840,953 B2  
APPLICATION NO. : 10/033951  
DATED : January 11, 2005  
INVENTOR(S) : Jonathan Martinek Page 1 of 1

It is certified that error appears in the above-identified patent and that said Letters Patent is hereby corrected as shown below:

Claim 2:

Line 8, "from the tin"

should read

-- from the tip --.

Signed and Sealed this

Fifth Day of August, 2008

JON W. DUDAS  
*Director of the United States Patent and Trademark Office*

UNITED STATES PATENT AND TRADEMARK OFFICE
CERTIFICATE OF CORRECTION

PATENT NO.         : 6,840,953 B2  
APPLICATION NO. : 10/033951  
DATED                  : January 11, 2005  
INVENTOR(S)        : Jonathan Martinek Page 1 of 1

It is certified that error appears in the above-identified patent and that said Letters Patent is hereby corrected as shown below:

Claim 2:

Column 6, Line 26, "from the tin"

should read

-- from the tip --.

This certificate supersedes the Certificate of Correction issued August 5, 2008.

Signed and Sealed this

Twenty-sixth Day of August, 2008

JON W. DUDAS  
*Director of the United States Patent and Trademark Office*